United States Patent

Kass et al.

[11] Patent Number: 6,090,047
[45] Date of Patent: Jul. 18, 2000

[54] ASSESSING CARDIAC CONTRACTILITY AND CARDIOVASCULAR INTERACTION

[75] Inventors: David A. Kass, Columbia; Hideaki Senzaki; Chen-Huan Chen, both of Baltimore, all of Md.

[73] Assignee: Johns Hopkins University, School of Medicine, Baltimore, Md.

[21] Appl. No.: 08/962,847

[22] Filed: Nov. 3, 1997

Related U.S. Application Data

[60] Provisional application No. 60/030,184, Nov. 4, 1996.

[51] Int. Cl.[7] .................................................. A61N 5/00
[52] U.S. Cl. ........................................ 600/485; 600/481
[58] Field of Search .............................. 600/526, 485, 600/486, 490, 493, 527–528, 481, 479, 483–484, 300–301, 500–504; 128/897–925

[56] References Cited

U.S. PATENT DOCUMENTS

| | | | |
|---|---|---|---|
| 4,535,774 | 8/1985 | Olson | 128/419 |
| 4,877,035 | 10/1989 | Bogen et al. | 128/673 |
| 5,107,838 | 4/1992 | Yamaguchi | 128/653.2 |
| 5,199,438 | 4/1993 | Pearlman | 128/670 |
| 5,274,549 | 12/1993 | Almasi | 364/413.07 |
| 5,390,679 | 2/1995 | Martin | 128/673 |
| 5,417,717 | 5/1995 | Salo et al. | 607/18 |
| 5,423,326 | 6/1995 | Wang et al. | 128/713 |
| 5,445,159 | 8/1995 | Cheng | 128/672 |
| 5,450,850 | 9/1995 | Iinuma | 128/661.09 |
| 5,634,467 | 6/1997 | Nevo | 128/672 |

FOREIGN PATENT DOCUMENTS

| | | | |
|---|---|---|---|
| 0 420 085 | 4/1991 | European Pat. Off. | A61B 5/021 |
| 0 651 970 | 10/1995 | European Pat. Off. | A61B 5/029 |

OTHER PUBLICATIONS

Igarashi, et al., "Assessment of Slope of End–Systolic Pressure–Volume Line of In Situ Dog Heart", Am. J. Physiol. 250 (Heart Circ. Physiol. 19), 1986, pp. H685–H692.

Sunagawa, et al., "Left Ventricular Interaction with Arterial Load Studied in Isolated Canine Ventricle", Am. J. Physiol. 245 (Heart Circ. Physiol. 14), 1983, pp.H773–H780.

Kass, et al., From 'Emax' to Pressure–Volume Relations: A Broader View, *Circulation*, Jun., 1988, vol. 77, No. 6. pp. 1203–1212.

Kass, et al., "Use of a Conductance (Volume) Catheter and Transient Inferior Vena Caval Occulsion for Rapid Determination of Pressure–Volume Relationships in Man", Catheterization and Cardiovascular Diagnosis, 1988, vol. 15, pp. 192–202.

Senzaki, et al., "Single–Beat Estimation of End–Systolic Pressure–Volume Relation in Humans", Circulation, vol. 94, No. 10, Nov. 15, 1996, pp. 2497–2506.

(List continued on next page.)

*Primary Examiner*—Cary O'Connor
*Assistant Examiner*—Michael Astorino
*Attorney, Agent, or Firm*—Cushman Darby & Cushman IP Group of Pillsbury Madison & Sutro LLP

[57] ABSTRACT

A novel method for estimating the end-systolic pressure-volume relationship (ESPVR) is presented. The method provides for accurate estimation of the ESPVR from a single beat of the cardiac cycle. The method is based on normalized human time varying elastance curves $[E_N(t_N)]$. The ESPVR is estimated from one beat using PV data measured at normalized time $t_N$ and end-systole ($t_{max}$) to predict intercept:

$$V_{0(SB)} = \frac{[P_N(t_N) \times V(t_{max}) - V(t_N) \times E_N(t_N)]}{[P_N(t_N) - E_N(t_N)]}$$

and slope:

$E_{max(SB)} = P(t_{max})/[V(t_{max}) - V_{0(SB)}]$. The present invention provides a method for ESPVR estimation which is non-invasive and particularly applicable for bedside applications.

31 Claims, 10 Drawing Sheets

OTHER PUBLICATIONS

Sunagawa, et al., "Estimination of the Hydromotive Source Pressure from Ejecting Beats of the Left Ventricle", *IEEE Transactions on Biomedical Engineering,* vol. BME–27, No. 6, Jun. 1980, pp. 299–305.

Takeuchi, et al., "Single–Beat Estimation of the Slope of the End–Systolic Pressure–Volume Relation in the Human Left Ventricle", *Circulation,* vol. 83, No. 1, Jan. 1991, pp. 202–212.

Sunagawa, et al., "Optimal Arterial Resistance for the Maximal Stroke Work Studied in Isolated Canine Left Ventricle", Circulation Research, vol. 56, No. 4, Apr. 1985, pp. 586–595.

Kass, et al., "Pressure–Volume Analysis as a Method for Quantifying Simultaneous Drug (Amrinone) Effects on Arterial Load and Contractile State in Vivo", *JACC,* vol. 16, No. 3, Sep. 1990, pp. 726–732.

Feldman, et al., "Acute Cardiovascular Effects of OPC–18790 in Patients with Congestive Heart Failure", Circulation, vol. 93, No. 3, Feb. 1996, pp. 474–483.

Suga, et al., Load Independence of the Instantaneous Pressure–Volume Ratio of the Canine Left Ventricle and Effects of Epinephrine and Heart Rate on the Ratio, *Circulation* Research, vol. XXXII, Mar. 1973, pp. 314–322.

Kass, "Ventriculo–Arterial Coupling: Concepts, Assumptions, and Applications", *Annals of Biomedical Engineering,* vol. 20, pp. 41–62, 1992.

Maughan, "The Use of the Pressure–Volume Diagram for Measuring Ventricular Pump Function", *Automedica,* 1989, vol. II, pp. 312–342.

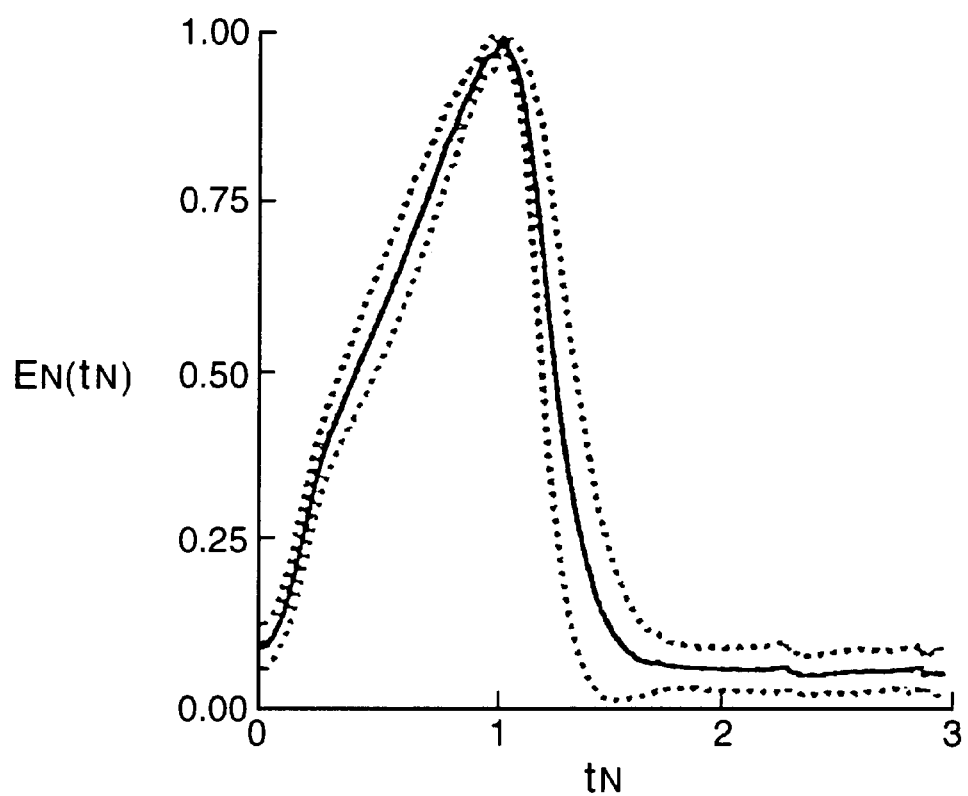

ASSESSING CARDIAC CONTRACTILITY AND CARDIOVASCULAR INTERACTION

This application claims the benefit of U.S. provisional application Ser. No. 60/030,184, filed on Nov. 4, 1996.

BACKGROUND OF THE INVENTION

1. Field of the Invention

The present invention relates generally to the field of cardiovascular assessment and performance. More specifically, the present invention relates to the field of non-invasive assessment of cardiac function based on pressure-volume relation analysis.

2. Description of the Related Art

The pressure-volume framework for assessing cardiac function, specifically the use of an end-systolic pressure-volume relationship (ESPVR) to assess cardiac contractile function is well-known. This analytic method is widely regarded as among the best means for defining cardiac chamber performance, and its interaction with the vascular (venous and arterial) systems. It can be used to both predict the behavior of the cardiovascular system during physiologic changes (such as sudden increases or decreases in blood pressure or circulating blood volume, and the influence of pharmacologic agents typically used to treat patients with heart disease. The major impediment to practical implementation of this analysis for clinical medicine is the difficulty in making all of the necessary measurements, and the requirement for invasive data. Recent advances in pressure-monitoring and Doppler imaging technology have provided methods to estimate arterial vascular properties non-invasively, but ESPVR characterization has remained much more difficult. A key contributor to this difficulty is the requirement of collecting data from many cardiac cycles for which the "loading" conditions (filling volumes, ejecting pressures) of the heart have been altered.

There have been attempts to estimate the ESPVR from single-cardiac cycles, however, these too do not provide a reliable and easily implemented method. The development of single-beat ESPVR estimation methods has been driven by the desire to simplify the loading procedures required to directly measure the ESPVR, and to avoid a need for continuous LV (left ventricular) volume data. In humans, the ESPVR is for all practical purposes a linear relation, which can be defined by a slope (termed either $E_{max}$, or the end-systolic elastance, $E_{es}$), and a volume axis intercept ($V_0$). The slope is a measure of chamber stiffness, and can be used to index contractility changes, while the volume axis intercept is a measure of chamber geometry, and can also be used to index contractile performance changes. Two basic approaches have been employed to date. The simplest and most frequently used has been to ignore $V_0$, and report the ratio of Pes/Ves (end-systolic pressure/volume ratio). This has shown to be inadequate since there can be marked variability in $V_0$, with often large non-zero intercepts in patients with infarction or dilated cardiomyopathy. An alternative method uses abrupt occlusion of the aorta during isovolumic contraction to determine peak isovolumic pressure, LV volume during ejection is estimated by integrating aortic flow and synchronizing the result with LV pressure. This method yields two pressure-volume points, one for the isovolumic contraction and one for the resting ejecting contraction, and by linking the two points by a line, one can estimate the slope $E_{max}$. A modification to this method was first suggested by Sunagawa et al, " . . . Instead of actually occluding the Aorta to determine isovolumic pressure and volume, an approach that could never be used clinically, these investigators provided a method to estimate this pressure-volume (PV) data by mathematical curve fitting of LV data measured during isovolumic contraction and relaxation phases of a steady-state ejecting beat." The fit predicts the peak pressure that would be generated in the absence of ejection, and by drawing a line between this theoretically derived "isovolumic" pressure-volume point and the measured end-systolic PV point from the same ejecting beat it yields the ESPVR estimate. This method has been tested in normal animals and in humans. While providing adequate results, the method required measurements of high fidelity LV pressure and is based on an arbitrary curve fit. Current non-invasive methods for assessing heart contractile function and the interaction between the heart and the arterial system are not easily implemented in a clinical environment.

SUMMARY OF THE INVENTION

It is an object of the present invention to provide a method for accurately predicting ESPVR from LV PV data that is easily extracted from a single heart beat.

It is a further object of the present invention to provide a method for accurately determining ESPVR which may be implemented non-invasively at the bedside.

It is another object of the present invention to provide a method to link the ESPVR predictions with non-invasive imaging and pressure monitoring technologies to generate clinical displays that provide a treating physician with information about current cardiovascular status and the likely effects of pharmacologic therapies on this status in patients with heart disease.

The end-systolic pressure-volume relation (ESPVR) is a valuable measure of ventricular systolic function for both clinical and experimental evaluations providing a very useful measure of contractile function. However, until now, in order to utilize ESPVR, it has been necessary to acquire data from multiple cardiac cycles at varying loads. This has limited our ability to utilize ESPVR. Acute ESPVR shifts primarily indicate inotropic change. The slope ($E_{max}$) measures end-systolic chamber stiffness, an important determinant of the influence of vascular loading on systolic pressure and flow generation. The ESPVR evolved from a linear time-varying elastance [E(t)] model of contraction, in which the left ventricle (LV) was considered to be an elastic structure that stiffens with a predictable time-course during the cardiac cycle.

The present invention utilizes a normalized time varying elastance model, E(t) curve (normalized both by amplitude and time to peak amplitude) to approximate the ESPVR from pressure and volume data relating to a single heart beat. Based upon collected data from patients reflecting a wide range of cardiovascular diseases as well as normal hearts, a normalized time-varying elastance curve was derived. The normalized E(t) function was defined based upon the elastance curve. The time interval between the R-wave of the electrocardiogram (ventricular activation) and the maximal P/V ratio ($t_{max}$) was determined, and real-time coordinates transformed to normalize time by this interval. The ESPVR estimate is based on two assumptions: 1) that the E(t) model is linear, and 2) that a single and constant volume axis intercept applies for a given cardiac cycle.

Based upon equations for a time-varying elastance, and specifically the ratio of instantaneous chamber elastance to maximal elastance measured at the end-systole, the ESPVR volume axis intercept was calculated. From this determination, the slope is calculated, providing the necessary numbers to estimate the ESPVR.

BRIEF DESCRIPTION OF THE DRAWINGS

FIG. 3 is a diagram illustrating group averaged normalized elastance curve [$E_N(t_N)$] from the underlying data supporting the present invention.

DETAILED DESCRIPTION OF THE PREFERRED EMBODIMENTS

It has been found that $E_N(t_N)$ curves are surprisingly similar among hearts, particularly during early contraction. Based on this observation, the present invention provides an arrangement (method and apparatus) for determining a good approximation of ESPVR using pressure, volume and timing data easily obtained from a single cardiac cycle. Our arrangement identifies both resting and acute changes in the ESPVR, is minimally sensitive to load, and yields a better estimate of directly measured relations than previously proposed techniques. Further, the present invention is adaptable to non-invasive analysis. As such, our invention makes it possible to more easily utilize ESPVR analysis in clinical medicine. The method has value not only for assessing acute and chronic changes in contractile function from therapeutic interventions, but also for predicting a patient's hemodynamic response to therapy.

The claimed arrangement for single-beat ESPVR estimation is based on the underlying premise of the time-varying elastance model of cardiac contraction that there is consistent $E_N(t_N)$, independent of heart rate, loading conditions, or contractility, that is scaled by both amplitude ($E_{max}$) and time ($t_{max}$) for a given ventricle. This further implies that the elastance relations are linear, and that they intersect at a common volume intercept.

The underlying data which was collected to confirm the basic hypothesis for the present invention established that the $E_N(t_N)$ curves were consistent among patients despite markedly varying underlying diseases and conditions, and that a single-beat estimation that assumed ESPVR linearity and constant $V_0$ yields very reasonable predictions. Establishing that $E_N(t_N)$ is consistent among hearts despite widely varying chronic disease states is what sets the present invention apart.

Figure 1A:
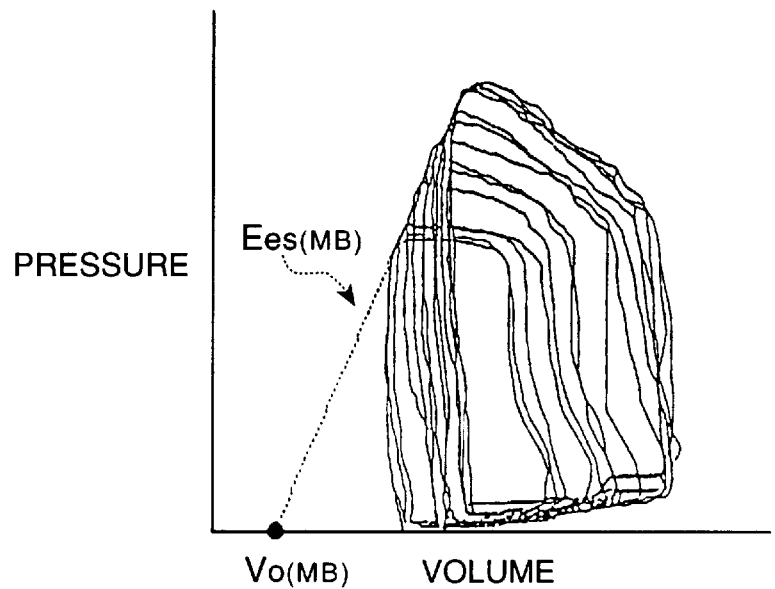
FIGS. 1A–1B are schematic diagrams explaining estimation of ESPVR slope and intercept.
Figure 1B:
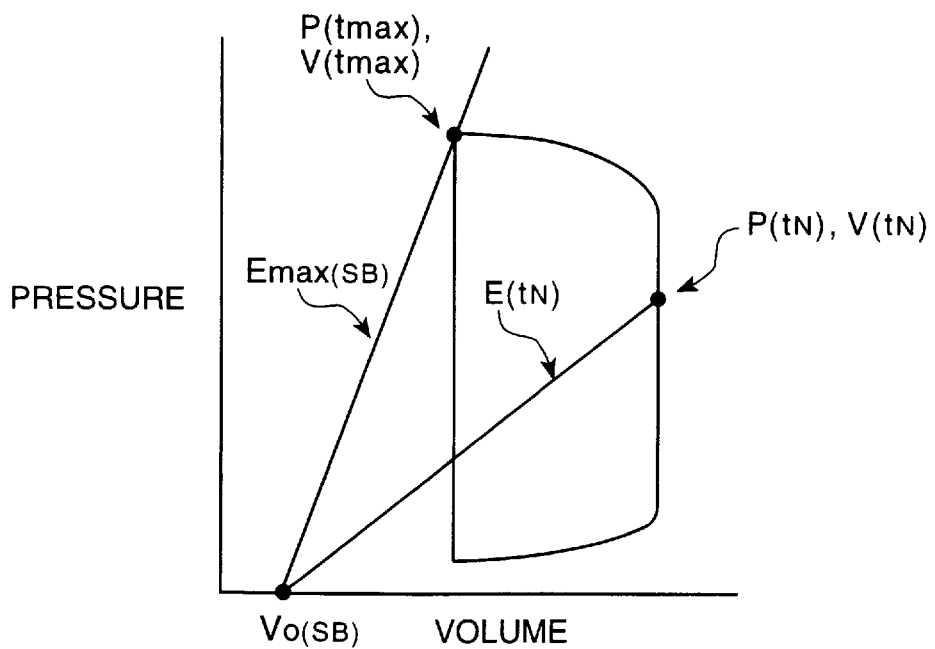

The present invention is based upon a study of nearly one hundred patients having a variety of heart conditions, including normal hearts and varying forms of chronic heart disease. Using these patients a reference or "gold standard" ESPVR was derived from multiple variably preloaded cardiac cycles measured during transient obstruction of IVC (inferior vena cava) inflow. Referring now to FIG. 1A, following the transient obstruction of the IVC, the blood return to the left-ventricle is decreased and a series of cardiac cycles with decreasing volume and pressure results. The ESPVR line connects the upper-left corners of the PV loops, which are the points of maximal pressure/(volume-$V_0$), where $V_0$ is the ESPVR volume-axis intercept. Following the determination of the ESPVR from multiple beats (MB), its parameters, the slope $E_{max(MB)}$, and the volume axis intercept $V_{0(MB)}$, are directly calculated. FIG. 1B presents how pressure-volume data from a single beat (SB) loop, which is either measured from one cardiac cycle or averaged from several cardiac cycles during steady state, are used by the current invention to estimate the ESPVR parameters. Based on two point on the PV loop, at times $t_N$ and $t_{max}$, the slope $E_{max(SB)}$ and intercept $V_{0(SB)}$ are estimated as detailed below.

To derive the normalized time-varying elastance curve, PV data from 3 to 5 sequential steady-state beats were signal averaged to yield a PV loop. Time-varying elastance [E(t)] was defined as the instantaneous ratio of $P(t)/[V(t)-V_{0(MB)}]$, using $V_{0(MB)}$ from prior multiple-beat ESPVR analysis. The maximal value of E(t) [$E_{max(SB)}$] and the time to achieve $E_{max(SB)}$ referenced from the R-wave of the electrocardiogram ($t_{max}$), were both determined. The normalized E(t) function was then defined as:

$$E_N(t_N)=E(t_N)/E_{max(SB)} \qquad \text{Eq. 1}$$

where $$t_N=t/t_{max} \qquad \text{Eq. 2}$$

To combine $E_N(t_N)$ relations, each curve was re-sampled at 200 equispaced intervals using linear interpolation, and the results averaged for each patient and/or hemodynamic group. A total mean $E_N(t_N)$ curve was obtained by averaging the results.

The present invention provides a method for single-beat ESPVR estimation, characterized by a linear slope $E_{max(SB)}$ and a volume-axis intercept $V_{0(SB)}$. FIG. 1B illustrates schematically the estimation method of the present invention. For each steady-state cardiac cycle, $t_{max}$ (the time between the R-wave and the maximal P/V ratio) is first determined, and the time coordinates are transformed to normalized time $t_N$, utilizing Eq. 2. PV data is then measured at times $t_N$ [$P(t_N)$ and $V(t_N)$] and $t_{max}$ [$P(t_{max})$, $V(t_{max})$], using linear interpolation. The ESPVR estimate is based on two assumptions: 1) that the E(t) model is linear; and 2) that a single volume axis intercept ($V_{0(SB)}$) applies for a given cardiac cycle. Using the definition for time-varying elastance E(t), chamber elastance at time $t_N$ is:

$$E(t_N)=P(t_N)/[V(t_N)-V_{0(SB)}] \qquad \text{Eq. 3}$$

and elastance at time $t_{max}$ is:

$$E(t_{max}) = E_{max(SB)} = P(t_{max})/[V(t_{max}) - V_{0(SB)}] \quad \text{Eq. 4}$$

As established, the ratio of $E(t_N)/E_{max(SB)}$ equals $E_N(t_N)$. Therefore, combining Eqs. 1, 3 and 4 the volume-axis intercept is obtained as:

$$V_{0(SB)} = \frac{[P_N(t_N) \times V(t_{max}) - V(t_N) \times E_N(t_N)]}{[P_N(t_N) - E_N(t_N)]} \quad \text{Eq. 5}$$

where $P_N(t_N) = P(t_N)/P(t_{max})$. Once $V_{0(SB)}$ is calculated, $E_{max(SB)}$ is determined from Eq. 4.

Figure 2A:
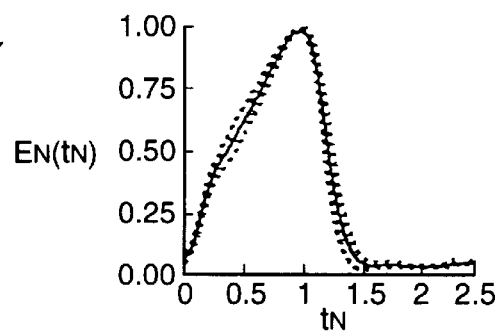
FIGS. 2A–2H are diagrams of normalized elastance [$E_N(t_N)$] curves for various patient groups and/or test condition for the underlying data supporting the present invention.
Figure 2B:
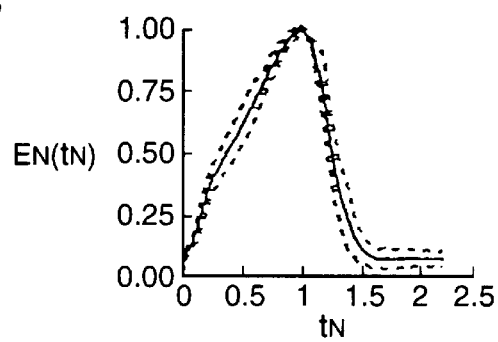
Figure 2C:
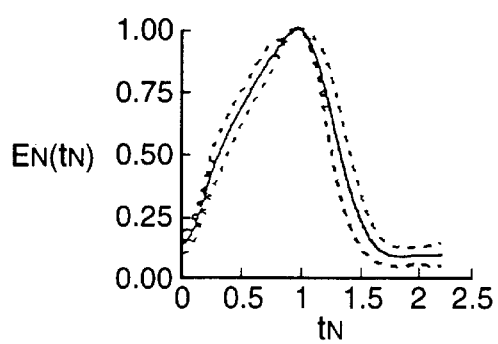
Figure 2D:
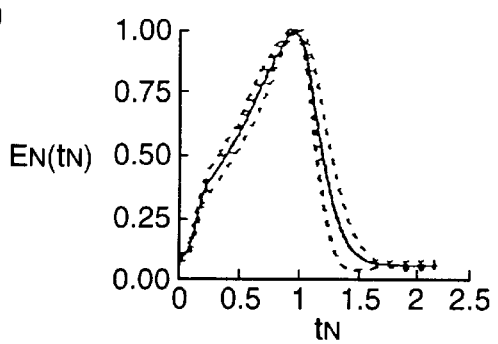
Figure 2E:
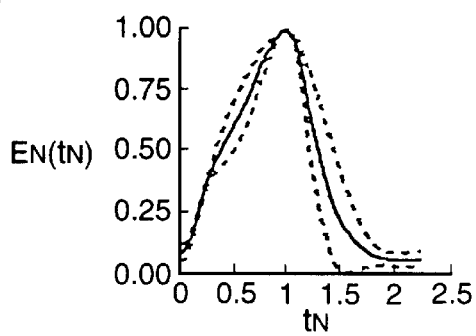
Figure 2F:
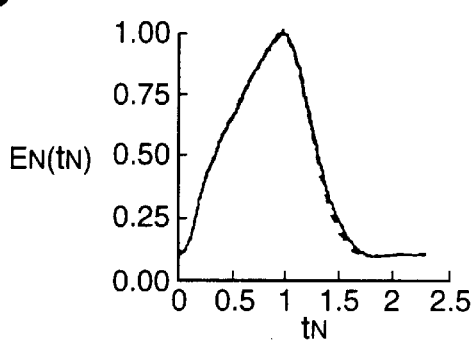
Figure 2G:
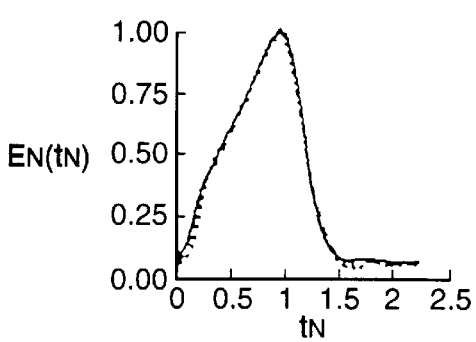
Figure 2H:
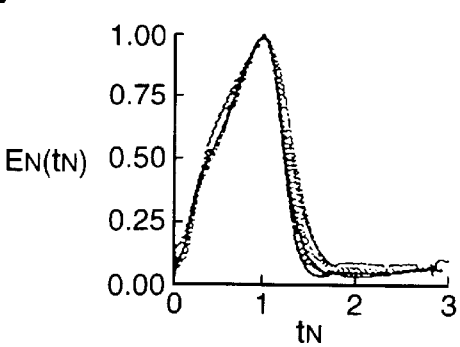

The results of the underlying study confirm the method of the present invention. With respect to the normalized elastance curve, $E_N(t_N)$, FIG. 2 displays averaged $E_N(t_N)$ curves for patients with normal hearts (A), and those with hypertrophy, (B), dilated cardiomyopathy, (C), coronary disease (D), and post-infarction aneurysm (E). The solid line is the mean and the dashed lines show ±1 Standard Deviation (SD). There is relatively little variance about the mean for each $E_N(t_N)$ curve in the various patient groups, particularly during the initial contraction phase (prior to the first inflection point). Furthermore, the mean $E_N(t_N)$ curves for the different groups were very similar, despite marked differences in preload, afterload, contractility and chronic disease. This is shown in FIG. 2H in which the curves are superimposed. $E_N(t_N)$ curves measured before or after positive inotropic stimulation (FIG. 2F, $E_{max}$ from 1.5±0.5 to 2.7±0.9) or artrial tachycardia pacing (FIG. 2G, HR at 76±10, 99±9 and 130±12 min$^{-1}$) were virtually superimposable. The phase with the least variance is early contraction (isovolumic phase), while that with the largest occurs during late relaxation. The net averaged $E_N(t_N)$±1 standard deviation (SD) curve is shown in FIG. 3.

Figure 4A:
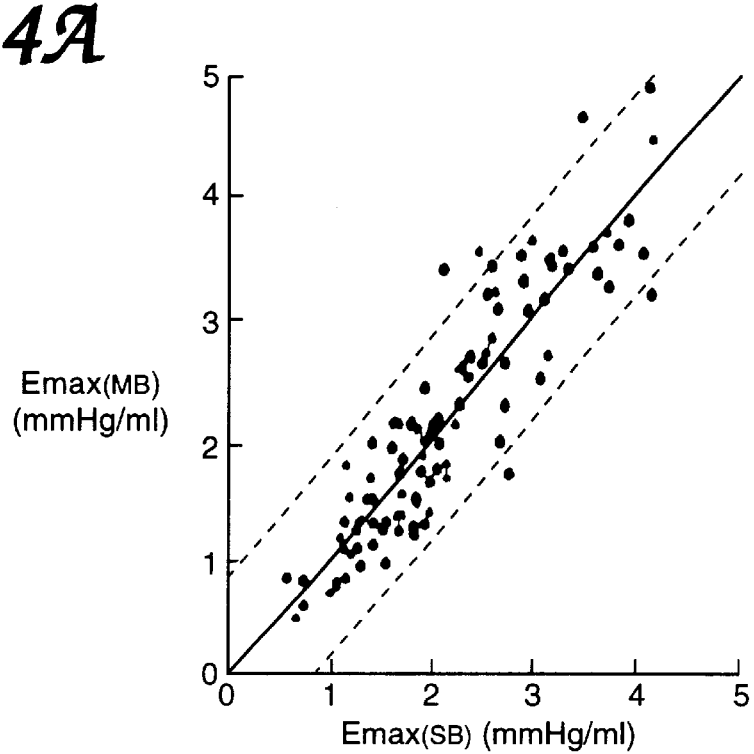
FIGS. 4A–4B show comparisons between measured values based on underlying patient studies and values determined by the present invention.
Figure 4B:
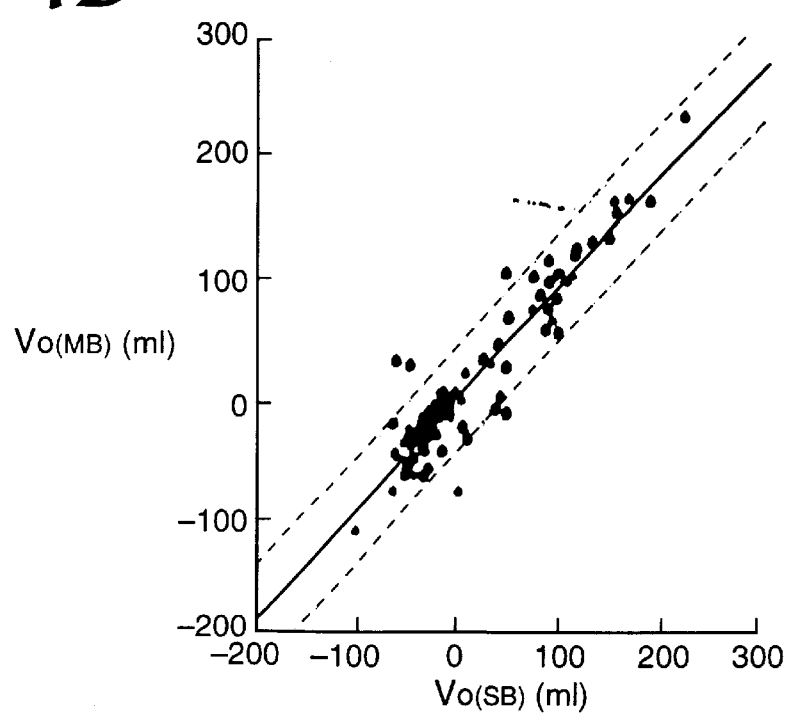
Figure 4C:
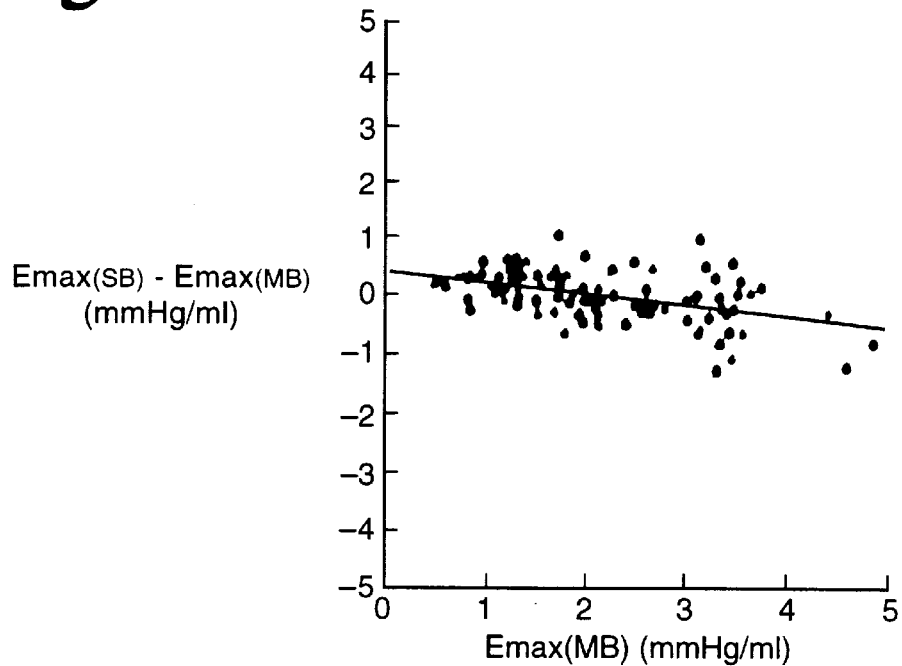
Figure 4D:
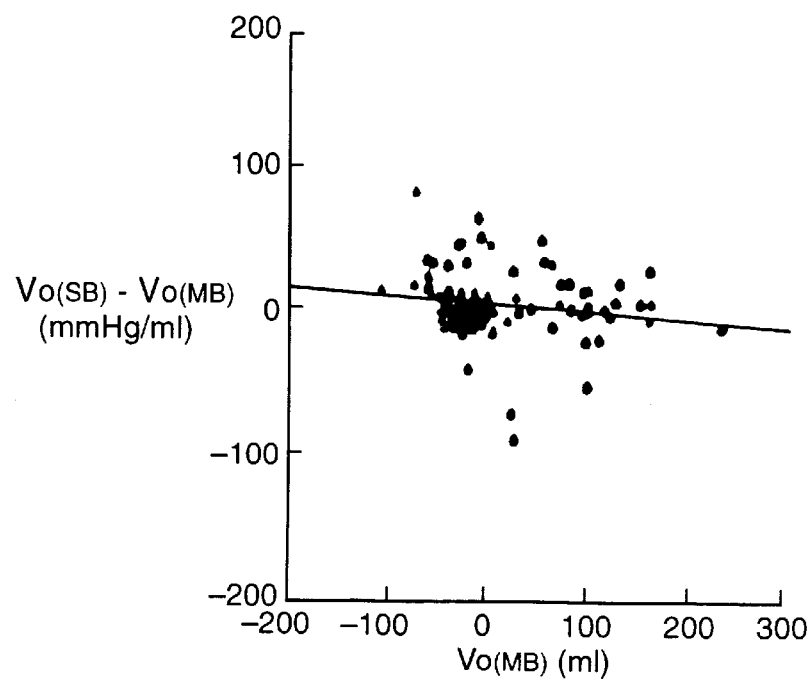

The results of the underlying study also establish the consistency of $E_N(t_N)$ supporting the method of the present invention for single-beat ESPVR estimation. While Eqs. 4 and 5 yield $V_{0(SB)}$ and $E_{max(SB)}$ estimates for any time $t_N$, it is preferable to select a $t_N$ when the physiologic variance in $E_N(t_N)$ is minimal. From FIG. 3, this occurs during early contraction. In addition, Eq. 5 reveals $V_{0(SB)}$ to be a hyperbolic function of $E_N(t_N)$ with a vertical asymptote at $E_N(t_N) = P_N(t_N)$. If $t_N$ (and $E_N(t_N)$) is selected near this value, then small errors will result in greater instability of the $V_{0(SB)}$ estimate. The optimal $t_N$ is one that minimizes both physiologic and mathematical variances. It is preferred that $t_N$ lie between 0.25 and 0.35. FIG. 4 displays results comparing directly measured values for the slope and intercept of the ESPVR with those values predicted by the current invention. FIG. 4A compares $E_{max}$ and $V_0$ estimated with the new single beat method ($E_{max(SB)}$ and $V_{0(SB)}$) with the "gold standard" estimation based on multiple beats ($E_{max(MB)}$ and $V_{0(MB)}$). The solid line is the linear regression line, and the dashed lines represent the 95% prediction intervals. Both sets of parameters were highly correlated, with regression line given by $E_{max(SB)} = 1.01 \times E_{max(MB)} + 0.03$, correlation coefficient r=0.9, standard error of estimate is 0.42. FIG. 4B presents the difference between the single beat and multiple beat estimations as function of the multiple beat estimations, and shows minimal dependence between the difference and the "gold reference" values of $E_{max}$ and $V_0$. The new method provides good predictive value, with a small standard error of the estimate, and regression slope and intercept that are very close to 1.0 and 0.0 respectively.

The ability to provide accurate non-invasive ESPVR estimation is particularly desirable. Clinical evaluation of ventricular function and ventricular-arterial interaction is particularly useful when employed as part of the chronic assessment of heart disease. The ability to make measurements non-invasively is valuable, since repeated evaluations over time generally provide the most insight, and these measurements are impractical if invasive data is required. Since the method of the present invention provides ESPVR estimation which incorporates data near the end of isovolumic contraction, it is particularly suitable for non-invasive assessment. Echocardiography or nuclear ventriculography can provide end-systolic and end-diastolic chamber volumes, while arterial cuff pressures provide diastolic and systolic pressures. Timing of the onset of ejection and end ejection can be obtained noninvasively by Doppler cardiography, by Phonocardiography, or other methods.

The ability to incorporate parameters which may be measured noninvasively provides a significant advantage to the present invention. $E_{max(SB)}$ may be estimated using Aortic pressure data. By selecting $t_N$ to occur at the onset of cardiac ejection then: $V(t_N) = EDV$, and $P(t_N) = A_o P_{DIA}$, the Aortic diastolic pressure. The end-systolic pressure, or $P(t_{max})$ could be estimated from the arterial systolic pressure by:

$$P(t_{max}) = P_{es} = (0.9 \times A_o P_{SYS}) \quad \text{Eq. 6}$$

Therefore, from arterial systolic and diastolic pressures, and values for ESV and EDV, each being measurable non-invasively, $V_{0(SB)}$ can be estimated by:

$$V_{0(SB)-AOP} = \frac{[A_o P_{DIA} \times ESV/(0.9 \times A_o P_{SYS}) - EDV \times E_N(t_N)]}{[A_o P_{DIA}/(0.9 \times A_o P_{SYS}) - E_N(t_N)]} \quad \text{Eq. 7}$$

and $$E_{max(SB)-AOP} = (0.9 \times A_o P_{SYS})/(ESV - V_{0(SB)}) \quad \text{Eq. 8}$$

Figure 5:
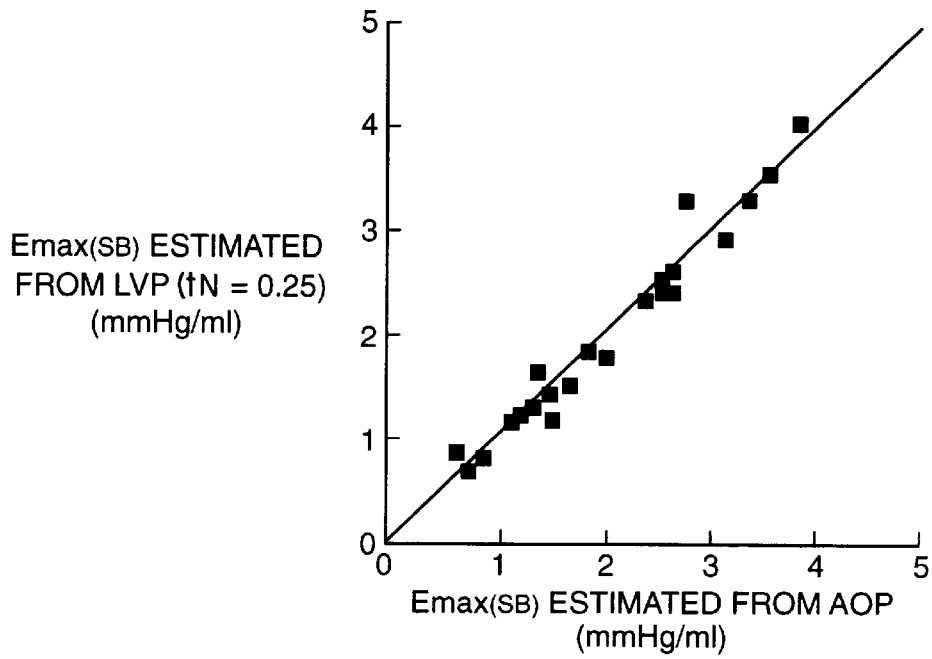
FIG. 5 compares a single-beat ESPVR slope estimation using invasive arterial pressure data and ventricular pressure data.

For an analysis based on arterial pressures, $t_{max}$ is calculated as the time between the R-wave of the electrocardiogram and the time of end-systole, which can be approximated by a time when arterial pressure declined by 10% of peak or by a time of end of ejection. Further, $t_N$ is the normalized time at the upstroke of arterial pressure (i.e. diastolic pressure) and $E_N(t_N)$ is determined at this time based on the previously derived averaged $E_N(t_N)$ curve, and the value is utilized in Eq. 7. FIG. 5 illustrates that with accurate measurements and timing, this substitution yields excellent agreement.

Figure 6A:
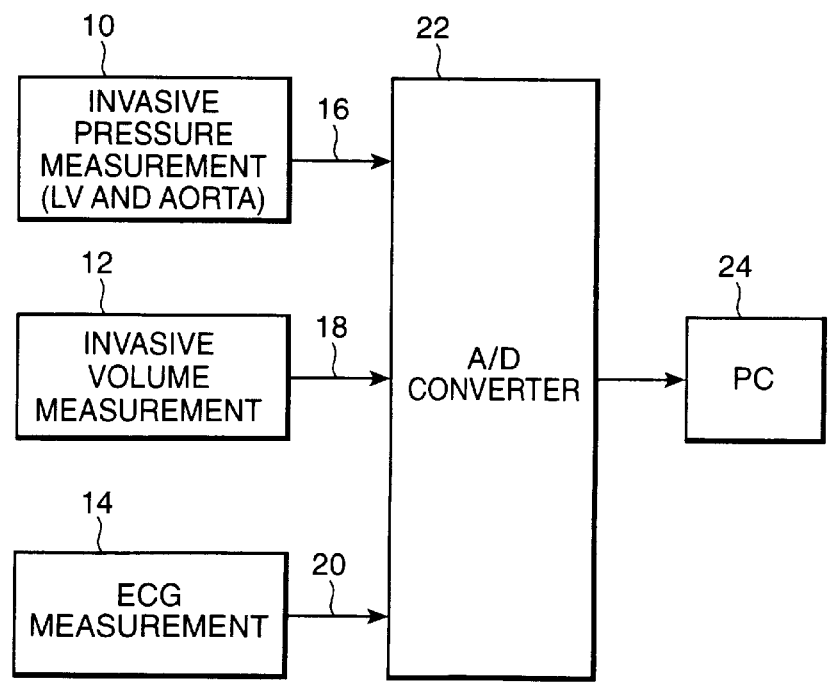
FIG. 6A illustrates a first embodiment of the invention which measures pressure and volume using invasive methods.

The invention can be used for the estimation of the ESPVR from either invasive or non-invasive measurements. One preferred embodiment is for use in the catheterization laboratory, where invasive pressure-volume measurements are generally recorded. Referring now to FIG. 6A, the apparatus includes a high fidelity invasive pressure measurement system (10) which provides a continuous measurement of the left-ventricular blood pressure but preferably provides also the aortic blood pressure. Catheters with dual micromanometer sensors, or single sensors that provide these signals are readily available (e.g. catheter model SPC-320, Millar Instruments, USA), as are the transducers and interface electronics to pass these signals to all current commercial catheterization laboratory hemodynamic recording systems (e.g. Q-Cath, Quinton Instrument Company, USA). Secondly, the apparatus involves an invasive volume measurement system (12) (this can be based on intraventricular conductance measurement system like Sigma V, CardioDynamics, the Netherlands, which gets the conductance measurements through conductance catheter, e.g. SSD-767, Millar Instruments, USA), that yields a continuous left ventricular volume signal. Third, is a standard electrocardiographic monitoring system (14) that provides a continuous analog ECG signal from a selected lead configuration, and is typically part of the commercial catheterization laboratory hemodynamic recording systems.

The pressure (16), volume (18) and the electrocardiogram (20) analog signals are digitized in real-time by a standard A/D board (22) (e.g. AT-MIO-16E-10, National Instruments, USA), and are displayed in real-time as well as recorded to computer memory using a standard personal computer (24) (e.g. Pentium 166 MHz PC, Gateway 2000, USA). The signals can be displayed using signal acquisition software such as provided by LabView 4 (National Instruments, USA) or by use of custom designed software.

Figure 6B:
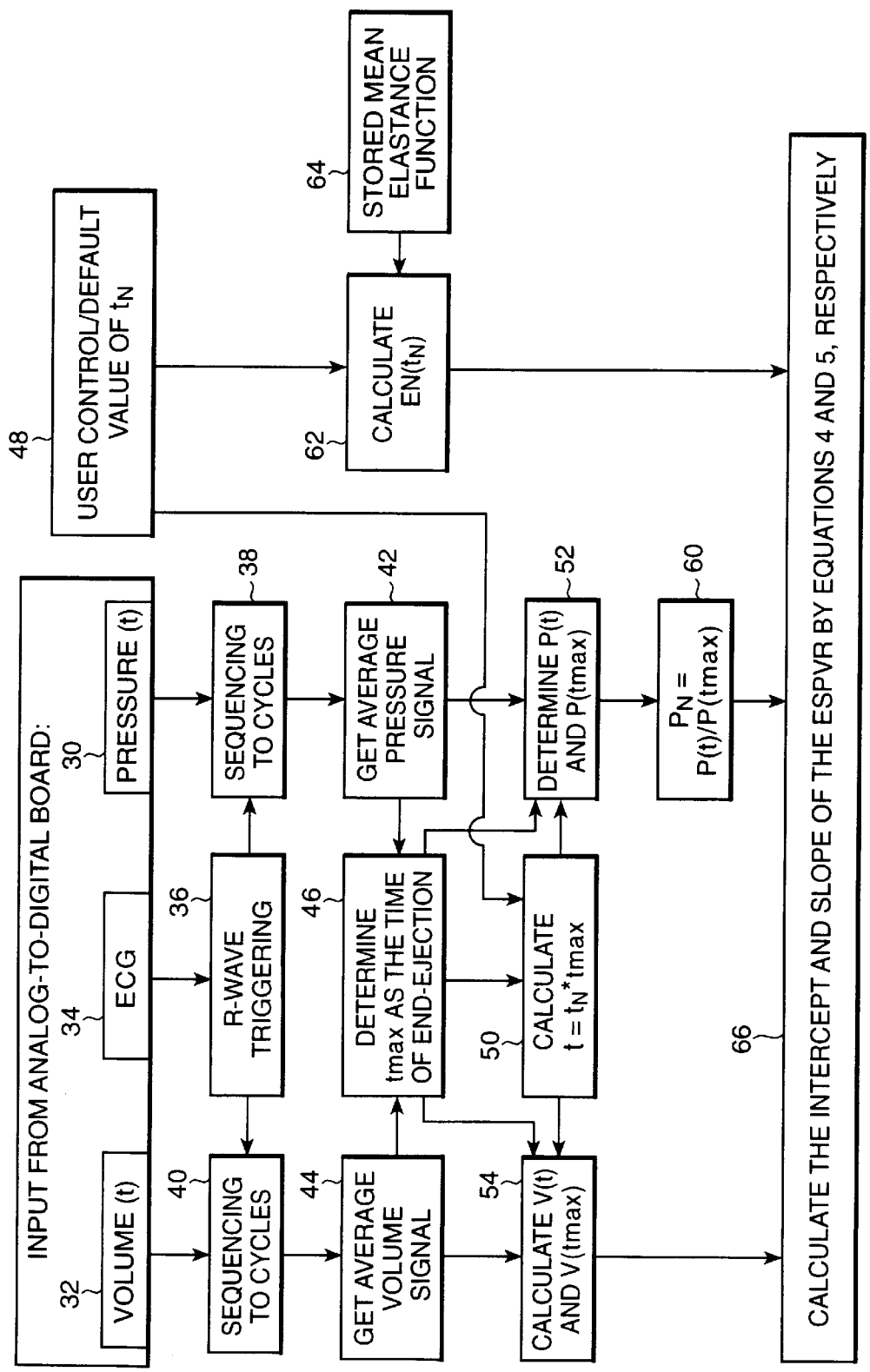
FIG. 6B explains the flow of data and the data processing that is carried out according to the first embodiment of the invention.

Referring now to FIG. 6B, the analysis of the digitized pressure (30), volume (32) and ECG (34) signals by the personal computer (24) is schematically presented and explained below.

Pressure (30) and volume (32) signals are recorded during several cardiac cycles (typically 3–5 cycles), ideally under conditions of quiet end-expiration to minimize signal noise. The onset of each cardiac cycle is determined by identifying the R-wave (36) of the ECG (34) through standard triggering modes such as thresholding of the ECG signal or its derivative. Based on the identification of the R-wave (36), the digitized pressure (30) and volume (32) signals are sequenced into pressure and volume signals of separate cardiac cycles. The pressure (38) and volume (40) signals from the separate cardiac cycles are group averaged to yield a mean pressure (42) and mean volume (44) representing the pressure and volume change over a cardiac cycle. From the average pressure (42) and average volume (44) data, the analysis program identifies the occurrence of end-ejection, based on well known physiologic features of these signals (for example, the end-ejection point can be identified from the volume signal as the point where there is no more volume decrease due to ejection, or it can be identified as the point where the aortic pressure and the ventricular pressure deviate following the closure of the aortic valve). The time interval between the occurrence of the R-wave (36) and end of ejection is denoted $t_{max}$ (46).

A default value or user-controlled value of the normalized time $t_N$ (48), which from experimental data should be within the range of 0.25 to 0.35, is used to calculate the absolute time "t" (50) which corresponds to the normalized time $t_N$. The absolute time "t" is calculated by rearranging Equation 2 to the form: $t=t_N \times t_{max}$. The pressures (52) and volumes (54) corresponding to times "t" (50) and "$t_{max}$" (46) are calculated by interpolation from the averaged pressure (42) and volume (44) data. The pressure at time "t" is normalized by the pressure at time $t_{max}$ and the normalized pressure is denoted $P_N(t_N)$ (60). The volume at absolute time "t", which corresponds to normalized time $t_N$ is denoted $V(t_N)$. The volume at time $t_{max}$ is denoted $V(t_{max})$.

The normalized elastance function for time $t_N$, namely $E_N(t_N)$ (62) is determined from the stored mean elastance function (64). For example, if the mean elastance function is stored in tabulated form, a linear interpolation can be used to find the $E_N(t_N)$ from the nearest tabulated points. If the mean elastance function is stored as a formula (e.g. polynomial or Fourier fit), the $E_N(t_N)$ can be calculated directly.

Finally, the volume-axis intercept of the ESPVR is calculated by Equation 5, and the slope is calculated by Equation 4. The calculated slope and intercept of the ESPVR (66) are presented to the user as numerical values and by a graphic display as in FIG. 1.

Figure 7A:
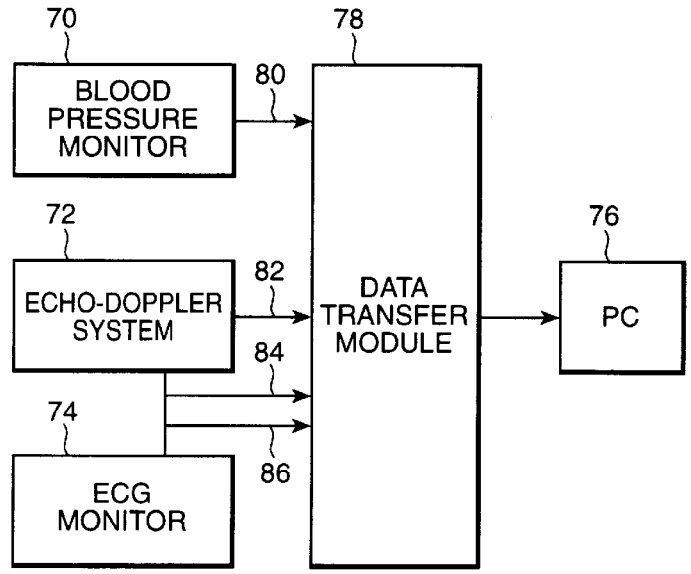
FIG. 7A illustrates a second embodiment of the invention in which pressure and volume are measured using non-invasive methods.

A second preferred embodiment is for use with non-invasive measurements. Referring now to FIG. 7A, the apparatus includes either a standard or a custom made non-invasive blood pressure monitor system (70) (e.g. Dynamap 1846SX, Critikon, USA). This monitor provides systolic and diastolic arterial blood pressure. Other alternative pressure signals would be continuous pulse tracings obtained by carotid tonometry (SPC350, Millar Instruments, USA), or by transformed radial arterial pulse tracings obtained by radial tonometry (Jentow, Collin Medical Instrument Corporation, USA). The second component (72) is a standard echo-Doppler system (e.g. Sonos 2500, Hewlett-Packard, USA). The commercially available echo-doppler systems provide clinically accepted estimates of ventricular end-diastolic volume (EDV), end-systolic volume (ESV) by standard analysis tools. An alternative option is to use a digital edge-detection algorithm, which is available as an option on some echo-doppler systems (e.g. Acoustic Quantification option, Sonos 2500, Hewlett-Packard, USA) to provide calibrated volume waveforms—in addition to the EDV and ESV values. Doppler flow measurement is used to derive stroke volume by time integral of the aortic velocity flow measurement multiplied by aortic cross sectional area, which is a standard clinical approach and is implemented as an analysis tool on most cardiologic echo-doppler systems. Lastly, the ejection fraction is derived from measurements using M-mode or directly from 2-dimensional imaging, both modes are standard on commercial echo-doppler systems. From the ejection fraction (EF) and stroke volume (SV), one calculates the end-diastolic (EDV) and end-systolic volumes (ESV) from: EDV=SV/EF; and ESV=SV(1-EF)/EF, based on the definitions of these parameters. These calculations are also provided as standard analysis tools by most cardiologic echo-doppler systems. Third, the system involves an electrocardiographic recorder or monitor device (74), which is a standard component of cardiologic echo-doppler systems like the Sonos 2500, Hewlett-Packard, USA.

The information that is transferred to the personal computer (76) for analysis is: arterial blood pressure measurements (80) from the blood pressure monitor (70) including aortic systolic ($AoP_{SYS}$) and diastolic ($AoP_{DIA}$) blood pressures; Volume measurements (82) from the echo-doppler system (72) are ventricular end-diastolic (EDV) and end-systolic (ESV) volumes; Time measurements are the time "t" (84) and the time "$t_{max}$" (86) which are measured with the echo-doppler system (72). The time "t" is measured between the R-wave of the electrocardiographic signal and the onset of blood ejection from the left ventricle. The time "$t_{max}$" is measured between the R-wave of the electrocardiographic signal and the termination of blood ejection from the left ventricle. The onset of ejection and the termination of ejection are determined by the opening and the closing of the aortic valve, respectively, which are demonstrated by M-mode echocardiography, or by the initiation and termination of a proximal aortic doppler flow waveform. These modes are standard on most cardiologic echo-doppler systems.

These measurements are transferred to the personal computer (76) by a data transfer module (78) which can be the keyboard of the personal computer (76) for manual entry of the parameters, or a standard serial communication or network connection for automated data transfer between the standard measurement devices (70, 72 and 74) and the computer (76).

The estimation of the slope and the intercept of the ESPVR from the non-invasive pressures, volumes and time intervals follows a similar procedure as described earlier for the invasive data. The main difference is that now the selection of the time "t" for the estimation process is limited to the region of the onset of ejection.

Figure 7B:
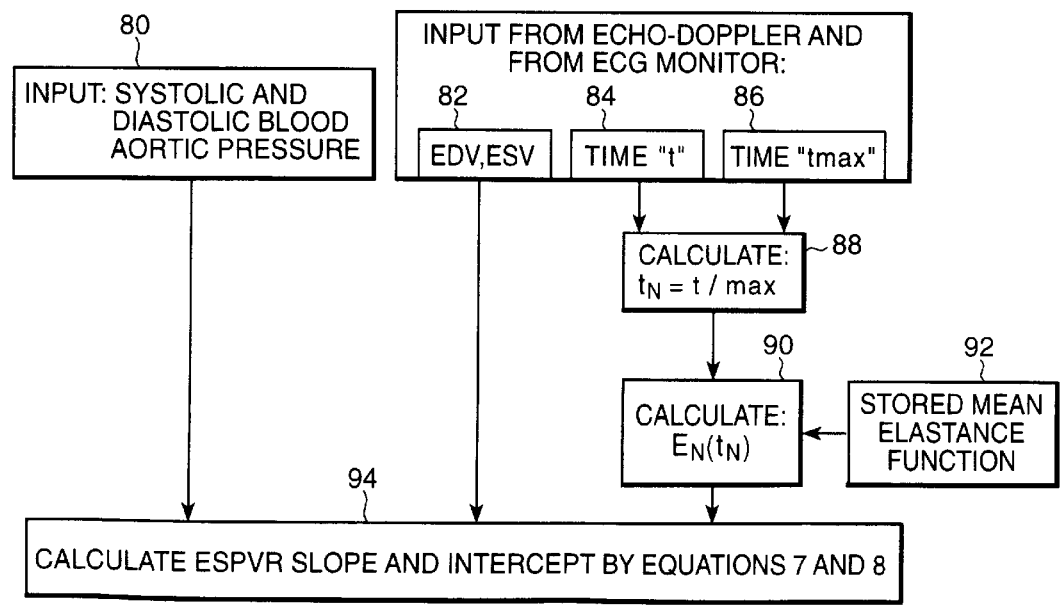
FIG. 7B explains the flow of data and the data processing that is carried out according to the second embodiment of the invention.

Referring now to FIG. 7B, the inputs to the personal computer analysis program are the systolic and diastolic aortic blood pressures (80), the end-diastolic and end-systolic ventricular volumes (82), the time "t" (84) and the time "$t_{max}$" (86).

The value of the normalized time $t_N$ (88) is calculated from Equation 2, based on the ratio between "t" (84) and "$t_{max}$" (86). The value of the mean elastance function at normalized time $t_N$ (90) is calculated from the stored mean elastance function (92) as detailed above for the first preferred embodiment.

Finally, the slope and intercept of the ESPVR (94) are calculated by equations 7 and 8.

The primary application of this technology is to provide a non-invasive cardiovascular assessment tool that can be applied in conjunction to existing devices linking echocardiographic imaging systems with automated arm-cuff and tonometric arterial pressure recording systems. Using pressure-volume and flow data that can be assessed non-invasively, the algorithm would predict the ESPVR, calculate an effective arterial elastance ($E_a = P_{es}/SV$), which is a correlated parameter that characterizes the arterial "load", and link these two parameters to predict cardiovascular status and the likely response to interventions based on known modeling equations. For example, the slope $E_{max}$, intercept $V_0$ of the ESPVR, end-diastolic chamber volume EDV, and value of arterial load $E_a$, can be combined to predict the stroke volume of the heart (Eq. 9), a common parameter that is important in managing patients with heart failure.

$$SV = E_{max} \times (EDV - V_0)/(E_{max} + E_a) \qquad \text{Eq. 9}$$

Figure 8A:
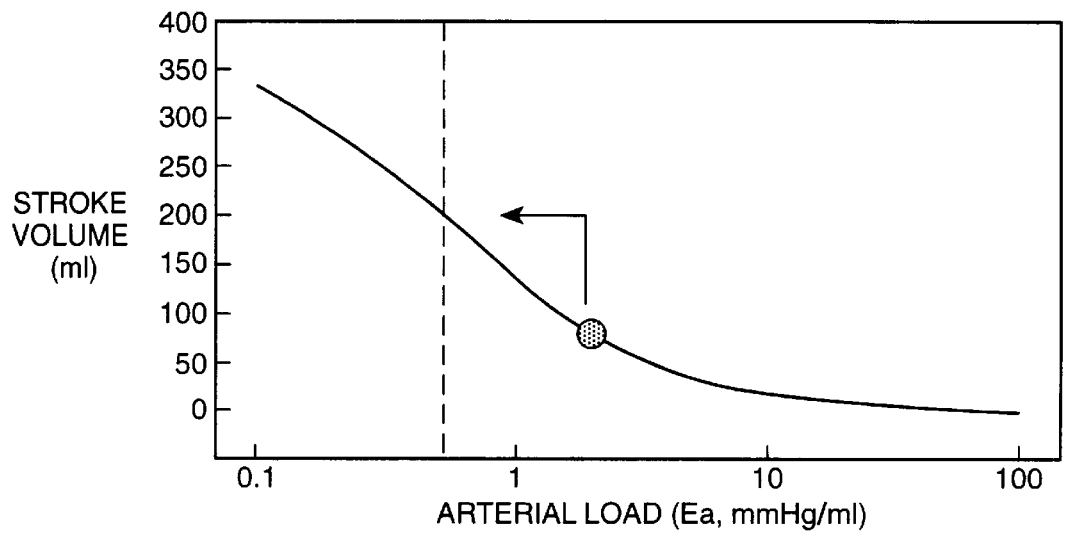
FIG. 8a is a diagram illustrating an application of the single-beat ESPVR estimation method of the present invention.
Figure 8B:
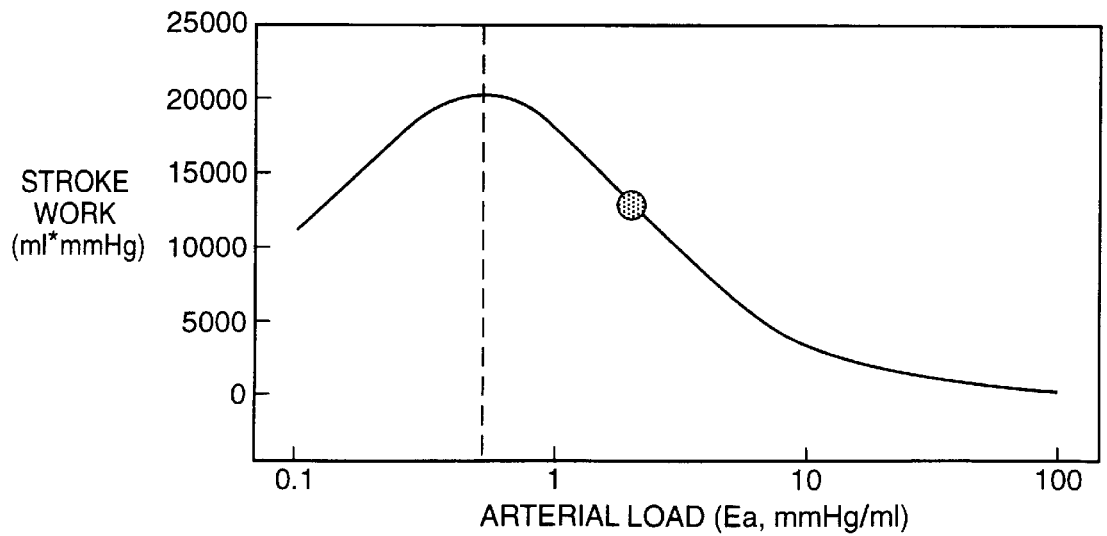
FIG. 8b is a diagram illustrating an application of the single-beat ESPVR estimation method of the present invention.

Analogous equations have been derived for cardiac work, efficiency, systolic pressure, ejection fraction, and other common hemodynamic variables. Each of these equations provides the dependent cardiovascular parameter as a function of circulating blood volume (EDV), effective arterial load ($E_a$) which also includes heart rate effects, contractility ($E_{max}$) and chamber remodeling ($V_0$). Curves describing each of the dependent parameters as a function of a varying independent variable can be displayed separately. For example, the equation above can be plotted as SV versus EDV, SV versus $E_a$, SV versus $E_{max}$, etc. and for each plot, the exact position of the patient's current status can be depicted. FIGS. 8A and 8B illustrates two such curves, where variables for cardiac stroke volume SV, and stroke work SW are plotted versus arterial loading ($E_a$) in FIGS. 8A and 8B, respectively. The current status of the patient is noted by the solid circle. The consequence of a 25% decline in arterial load, which could be obtained by vasodilator therapy, can be predicted for both parameters based on this framework. Thus, the physician can be shown a series of function curves, which dissect the integrated information embodied by the single-beat elastance calculations into more practical displays of the cardiovascular system. Repeat curves obtained on different office visits could be stored and displayed as temporal histograms to indicate chronic progress of clinical status. This will likely prove of great clinical value of the chronic management of heart failure patients.

What is claimed is:

1. A method of determining an end-systolic pressure-volume relationship (ESPVR) of a human heart during steady state operation of the heart and without any load changes, comprising steps of:

measuring a blood pressure of a left ventricle of the heart and producing a pressure signal indicative thereof;

measuring a volume of the left ventricle and producing a volume signal indicative thereof;

monitoring the heart to produce ECG timing signals indicative of its activity;

analyzing the pressure, the volume and the timing signals based on a previously determined model of normalized elastance function for a normalized time $t_N$ to determine the ESPVR; and displaying the ESPVR.

2. A method according to claim 1, wherein the analyzing comprises performing the analyzing on a computer.

3. A method according to claim 2, wherein the pressure, the volume and the timing signals are digital signals.

4. A method according to claim 2, wherein the pressure signal, the volume signal and the timing signal are produced as analog signals, the method further comprising:

converting the analog signals to digital signals; and inputting the digital signals into the computer.

5. A method according to claim 1, wherein the analyzing comprises:

recording the pressure signal and the volume signal over at least one cardiac cycle;

identifying an R-wave of the ECG timing signal;

sequencing the pressure signals into pressure signals of separate ones of the at least one cardiac cycle based on an identification of the R-wave;

sequencing the volume signals into volume signals of the separate ones of the at least one cardiac cycle based on the identification of the R-wave;

group averaging the pressure signals of the separate ones of the at least one cardiac cycle to produce a mean pressure;

group averaging the volume signals of the separate ones of the at least one cardiac cycle to produce a mean volume;

identifying an occurrence of end-ejection based on one of the volume signal from the step of measuring the volume and the pressure signal from the step of measuring the blood pressure;

determining a time interval $t_{max}$ between an occurrence of the R-wave and the occurrence of end-ejection;

calculating an absolute time t based on the normalized time $t_N$ according to an equation $t = t_N \times t_{max}$;

determining a pressure at time t, P(t), and a pressure at time $t_{max}$, P($t_{max}$), based on the mean pressure;

determining a volume at time t, V(t), and a volume at time $t_{max}$, V($t_{max}$), based on the mean volume;

determining a normalized pressure $P_N(t_N)$ based on the P(t) and the P($t_{max}$);

calculating a normalized elastance function for the time $t_N$, $E_N(t_N)$, based on a stored mean elastance function;

calculating a volume-axis intercept $V_{0(SB)}$ of the ESPVR based on an equation $$V_{0(SB)} = \frac{[P_N(t_N) \times V(t_{max}) - V(t_N) \times E_N(t_N)]}{[P_N(t_N) - E_N(t_N)]}; \text{ and}$$

calculating a slope $E_{max(SB)}$ according to an equation $$E_{max(SB)} = P(t_{max})/[V(t_{max}) - V_{0(SB)}].$$

6. A method according to claim 5, wherein:

the measuring of the blood pressure includes measuring aortic blood pressure, and the identifying of an occurrence of end ejection is based on the blood pressure of the left ventricle and the aortic blood pressure.

7. A method according to claim 5, wherein:

the stored mean elastance function is stored in tabulated form, and the method further comprises using linear interpolation to find $E_N(t_N)$ from a nearest tabulated point.

8. A method according to claim 5, further comprising selecting a user-controlled value of the normalized time $t_N$, from which the absolute time t is calculated, from a range of about 0.25 to about 0.35.

9. A method according to claim 1, further comprising:

determining a time interval t between an R-wave of the ECG signal and an onset of blood ejection from the heart's left ventricle;

determining a time interval $t_{max}$ measured between the R-wave of the ECG signal and a termination of the blood ejection from the heart's left ventricle, wherein the step of analyzing the pressure, the volume, and the ECG timing signals comprises:

recording the blood pressure signal, the blood pressure signal including aortic systolic $A_oP_{SYS}$ and diastolic $A_oP_{DIA}$ blood pressures;

recording the volume signal, the volume signal including ventricular end-diastolic EDV and end-systolic ESV volumes;

calculating a normalized time $t_N$ from an equation $$t_N = t/t_{max};$$

calculating a normalized elastance function for the time $t_N$, $E_N(t_N)$, based on a stored mean elastance function;

estimating a volume-axis intercept $V_{0(SB)}$ of the ESPVR based on an equation $$V_{0(SB)\text{-}AOP} = \frac{[A_oP_{DIA} \times ESV/(0.9 \times A_oP_{SYS}) - EDV \times E_N(t_N)]}{[A_oP_{DIA}/(0.9 \times A_oP_{SYS}) - E_N(t_N)]};$$

estimating a slope $E_{max(SB)}$ based on an equation $$E_{max(SB)\text{-}AOP} = (0.9 \times A_oP_{SYS})/(ESV - V_{0(SB)});$$

wherein the onset and the termination of the blood ejection are determined by one of M-mode echocardiography and by initiation and termination of a proximal aortic Doppler flow waveform.

10. A method according to claim 9, wherein the time interval t is limited to a region of the onset of the blood ejection.

11. A method according to claim 1, wherein the measuring of the blood pressure comprises using an invasive pressure measurement system.

12. A method according to claim 1, wherein the measuring of the volume comprises using an invasive volume measurement system.

13. A method according to claim 1, wherein the monitoring of the human heart to produce the ECG signal comprises using an electrocardiographic monitoring system.

14. A method according to claim 1, wherein the measuring of the blood pressure comprises using a non-invasive blood pressure monitor.

15. A method according to claim 1, wherein the measuring of the volume comprises using an echo-Doppler system.

16. An apparatus for determining an end-systolic pressure-volume relationship (ESPVR) during steady state operation of a human heart and without any load changes, comprising:

a blood pressure monitor for measuring a blood pressure of a left ventricle of the human heart and producing a pressure signal indicative thereof;

a volume measurement system for measuring a volume of the left ventricular chamber and producing a volume signal indicative thereof;

an electrocardiograph monitor for monitoring the human heart and producing an ECG signal of the human heart;

a computer for receiving the pressure signal, the volume signal, and the ECG signal, the computer including:

means for determining the ESPVR based upon the pressure, the volume, and a timing derived from the ECG signal and determining the ESPVR.

17. An apparatus according to claim 16, wherein the determining means comprises:

means for recording the pressure signal and the volume signal over a plurality of cardiac cycles;

means for identifying an R-wave of the ECG timing signal;

means for sequencing the pressure signals into pressure signals of separate ones of the plurality of cardiac cycles based on an identification of the R-wave;

means for sequencing the volume signals into volume signals of the separate ones of the plurality of cardiac cycles based on the identification of the R-wave;

means for group averaging the pressure signals of the separate ones of the plurality of cardiac cycles to produce a mean pressure;

means for group averaging the volume signals of the separate ones of the plurality of cardiac cycles to produce a mean volume;

means for identifying an occurrence of end-ejection based on one of the volume signal from the step of measuring the volume and the pressure signal from the step of measuring the blood pressure;

means for determining a time interval $t_{max}$ between an occurrence of the R-wave and the occurrence of end-ejection;

means for calculating an absolute time t based on a normalized time $t_N$ according to an equation $t = t_N \times t_{max}$;

means for determining a pressure at time t, P(t), and a pressure at time $t_{max}$, $P(t_{max})$, based on the mean pressure;

means for determining a volume at time t, V(t), and a volume at time $t_{max}$, $V(t_{max})$, based on the mean volume;

means for determining a normalized pressure $P_N(t_N)$ based on the P(t) and the $P(t_{max})$;

means for calculating a normalized elastance function for the time $t_N$, $E_N(t_N)$, based on a stored mean elastance function;

means for calculating a volume-axis intercept $V_{0(SB)}$ of the ESPVR based on an equation $$V_{0(SB)} = \frac{[P_N(t_N) \times V(t_{max}) - V(t_N) \times E_N(t_N)]}{[P_N(t_N) - E_N(t_N)]}; \text{ and}$$

means for calculating a slope $E_{max(SB)}$ according to an equation $E_{max(SB)} = P(t_{max})/[V(t_{max}) - V_{0(SB)}]$.

18. An apparatus according to claim 16, wherein the determining means comprises:
   means for recording the blood pressure signal, the blood pressure signal including aortic systolic $A_oP_{SYS}$ and diastolic $A_oP_{DIA}$ blood pressures;
   means for recording the volume signal, the volume signal including ventricular end-diastolic EDV and end-systolic ESV volumes;
   means for calculating a normalized time $t_N$ from an equation $t_N = t/t_{max}$, where a time interval t is determined by the volume measurement system and the electrocardiograph monitor to be between an R-wave of the ECG signal and an onset of blood ejection from the heart's left ventricle, and is input to the computer, a time interval $t_{max}$ is determined by the volume measurement system and the electrocardiograph monitor to be between the R-wave of the ECG signal and a termination of the blood ejection from the heart's left ventricle, and is input to the computer;
   means for calculating a normalized elastance function for the time $t_N$, $E_N(t_N)$, based on a stored mean elastance function;
   means for estimating a volume-axis intercept $V_{0(SB)}$ of the ESPVR based on an equation $$V_{0(SB)-AOP} = \frac{[A_oP_{DIA} \times ESV/(0.9 \times A_oP_{SYS}) - EDV \times E_N(t_N)]}{[A_oP_{DIA}/(0.9 \times A_oP_{SYS}) - E_N(t_N)]};$$

means for estimating a slope $E_{max(SB)}$ based on an equation $E_{max(SB)-AOP} = (0.9 \times A_oP_{SYS})(ESV - V_{0(SB)})$.

19. An apparatus according to claim 16, wherein:
the blood pressure monitor comprises an invasive pressure measurement system.

20. An apparatus according to claim 16, wherein:
the blood pressure monitor comprises a non-invasive pressure measurement system.

21. An apparatus according to claim 16, wherein:
the volume measurement system comprises an invasive volume measurement system.

22. An apparatus according to claim 16, wherein:
the volume measurement system comprises a non-invasive volume measurement system.

23. An apparatus according to claim 16, wherein:
the volume measurement system comprises a non-invasive echo-Doppler system.

24. A method of determining an end-systolic pressure-volume relationship (ESPVR) of a human heart, comprising steps of:
   measuring a blood pressure of a left ventricle of the heart and producing a pressure signal indicative thereof;
   measuring a volume of the left ventricle and producing a volume signal indicative thereof;
   monitoring the heart to produce ECG timing signals indicative of its activity;
   analyzing the pressure, the volume and the timing signals based on a previously determined model of normalized elastance function for a normalized time $t_N$ to determine the ESPVR; and
   displaying the ESPVR, wherein:
   the analyzing comprises:
      recording the pressure signal and the volume signal over at least one cardiac cycle,
      identifying an R-wave of the ECG timing signal,
      sequencing the pressure signals into pressure signals of separate ones of the at least one cardiac cycle based on an identification of the R-wave,
      sequencing the volume signals into volume signals of the separate ones of the at least one cardiac cycle based on the identification of the R-wave,
      group averaging the pressure signals of the separate ones of the at least one cardiac cycle to produce a mean pressure,
      group averaging the volume signals of the separate ones of the at least one cardiac cycle to produce a mean volume,
      identifying an occurrence of end-ejection based on one of the volume signal from the step of measuring the volume and the pressure signal from the step of measuring the blood pressure,
      determining a time interval $t_{max}$ between an occurrence of the R-wave and the occurrence of end-ejection,
      calculating an absolute time t based on the normalized time $t_N$ according to an equation $t = t_N \times t_{max}$,
      determining a pressure at time t, P(t), and a pressure at time $t_{max}$, $P(t_{max})$, based on the mean pressure,
      determining a volume at time t, V(t), and a volume at time $t_{max}$, $V(t_{max})$, based on the mean volume,
      determining a normalized pressure $P_N(t_N)$ based on the P(t) and the $P(t_{max})$,
      calculating a normalized elastance function for the time $t_N$, $E_N(t_N)$, based on a stored mean elastance function,
      calculating a volume-axis intercept $V_{0(SB)}$ of the ESPVR based on an equation $$V_{0(SB)} = \frac{[P_N(t_N) \times V(t_{max}) - V(t_N) \times E_N(t_N)]}{[P_N(t_N) - E_N(t_N)]},$$

and
      calculating a slope $E_{max(SB)}$ according to an equation $E_{max(SB)} = P(t_{max})/[V(t_{max}) - V_{0(SB)}]$.

25. A method according to claim 24, wherein:
the measuring of the blood pressure includes measuring aortic blood pressure, and
the identifying of an occurrence of end ejection is based on the blood pressure of the heart's left ventricle and the aortic blood pressure.

26. A method according to claim 24, wherein:
the stored mean elastance function is stored in tabulated form, and the method further comprises using linear interpolation to find $E_N(t_N)$ from a nearest tabulated point.

27. A method according to claim 24, further comprising:
selecting a user-controlled value of the normalized time $t_N$, from which the absolute time t is calculated, from a range of about 0.25 to about 0.35.

28. A method of determining an end-systolic pressure-volume relationship (ESPVR) of a human heart, comprising steps of:
   measuring a blood pressure of a left ventricle of the heart and producing a pressure signal indicative thereof;
   measuring a volume of the left ventricle and producing a volume signal indicative thereof;

monitoring the heart to produce ECG timing signals indicative of its activity;

analyzing the pressure, the volume and the timing signals based on a previously determined model of normalized elastance function for a normalized time $t_N$ to determine the ESPVR; and displaying the ESPVR, wherein the method further comprises:

determining a time interval t between an R-wave of the ECG signal and an onset of blood ejection from the heart's left ventricle;

determining a time interval $t_{max}$ measured between the R-wave of the ECG signal and a termination of the blood ejection from the heart's left ventricle, wherein the step of analyzing the pressure, the volume, and the ECG timing signals comprises:

recording the blood pressure signal, the blood pressure signal including aortic systolic $A_oP_{SYS}$ and diastolic $A_oP_{DIA}$ blood pressures, recording the volume signal, the volume signal including ventricular end-diastolic EDV and end-systolic ESV volumes, calculating a normalized time $t_N$ from an equation $$t_N = t/t_{max},$$

calculating a normalized elastance function for the time $t_N$, $E_N(t_N)$, based on a stored mean elastance function;

estimating a volume-axis intercept $V_{0(SB)}$ of the ESPVR based on an equation $$V_{0(SB)-AOP} = \frac{[A_oP_{DIA} \times ESV / (0.9 \times A_oP_{SYS}) - EDV \times E_N(t_N)]}{[A_oP_{DIA} / (0.9 \times A_oP_{SYS}) - E_N(t_N)]},$$

estimating a slope $E_{max(SB)}$ based on an equation $$E_{max(SB)-AOP} = (0.9 \times A_oP_{SYS})/(ESV - V_{0(SB)}),$$

wherein the onset and the termination of the blood ejection are determined by one of M-mode echocardiography and by initiation and termination of a proximal aortic Doppler flow waveform.

29. A method according to claim 28, wherein the time interval t is limited to a region of the onset of the blood ejection.

30. An apparatus for determining an end-systolic pressure-volume relationship (ESPVR), comprising:

a blood pressure monitor for measuring a blood pressure of a left ventricle of a human heart and producing a pressure signal indicative thereof;

a volume measurement system for measuring a volume of the left ventricular chamber and producing a volume signal indicative thereof;

an electrocardiograph monitor for monitoring the human heart and producing an ECG signal of the human heart;

a computer for receiving the pressure signal, the volume signal, and the ECG signal, the computer including:

means for determining the ESPVR based upon the pressure, the volume, and a timing derived from the ECG signal and determining the ESPVR, wherein the determining means comprises:

means for recording the pressure signal and the volume signal over a plurality of cardiac cycles, means for identifying an R-wave of the ECG timing signal, means for sequencing the pressure signals into pressure signals of separate ones of the plurality of cardiac cycles based on an identification of the R-wave, means for sequencing the volume signals into volume signals of the separate ones of the plurality of cardiac cycles based on the identification of the R-wave, means for group averaging the pressure signals of the separate ones of the plurality of cardiac cycles to produce a mean pressure, means for group averaging the volume signals of the separate ones of the plurality of cardiac cycles to produce a mean volume, means for identifying an occurrence of end-ejection based on one of the volume signal from the step of measuring the volume and the pressure signal from the step of measuring the blood pressure, means for determining a time interval $t_{max}$ between an occurrence of the R-wave and the occurrence of end-ejection, means for calculating an absolute time t based on a normalized time $t_N$ according to an equation $t = t_N \times t_{max}$, means for determining a pressure at time t, P(t), and a pressure at time $t_{max}$, $P(t_{max})$, based on the mean pressure, means for determining a volume at time t, V(t), and a volume at time $t_{max}$, $V(t_{max})$, based on the mean volume, means for determining a normalized pressure $P_N(t_N)$ based on the P(t) and the $P(t_{max})$, means for calculating a normalized elastance function for the time $t_N$, $E_N(t_N)$, based on a stored mean elastance function, means for calculating a volume-axis intercept $V_{0(SB)}$ of the ESPVR based on an equation $$V_{0(SB)} = \frac{[P_N(t_N) \times V(t_{max}) - V(t_N) \times E_N(t_N)]}{[P_N(t_N) - E_N(t_N)]}, \text{ and}$$

means for calculating a slope $E_{max(SB)}$ according to an equation $$E_{max(SB)} = P(t_{max})/[V(t_{max}) - V_{0(SB)}].$$

31. An apparatus for determining an end-systolic pressure-volume relationship (ESPVR), comprising:

a blood pressure monitor for measuring a blood pressure of a left ventricle of a human heart and producing a pressure signal indicative thereof;

a volume measurement system for measuring a volume of the left ventricular chamber and producing a volume signal indicative thereof;

an electrocardiograph monitor for monitoring the human heart and producing an ECG signal of the human heart;

a computer for receiving the pressure signal, the volume signal, and the ECG signal, the computer including:

means for determining the ESPVR based upon the pressure, the volume, and a timing derived from the ECG signal and determining the ESPVR, wherein the determining means comprises:

means for recording the blood pressure signal, the blood pressure signal including aortic systolic $A_oP_{SYS}$ and diastolic $A_oP_{DIA}$ blood pressures, means for recording the volume signal, the volume signal including ventricular end-diastolic EDV and end-systolic ESV volumes, means for calculating a normalized time $t_N$ from an equation $t_N = t/t_{max}$, where a time interval t is determined by the volume measurement system and the electrocardiograph monitor to be between an R-wave of the ECG signal and an onset of blood ejection from the heart's left ventricle, and is input to the computer, a time interval $t_{max}$ is determined by the volume measurement system and the electrocardiograph monitor to be between the R-wave of the ECG signal and a termination of the blood ejection from the heart's left ventricle, and is input to the computer, means for calculating a normalized elastance function for the time $t_N$, $E_N(t_N)$, based on a stored mean elastance function, means for estimating a volume-axis intercept $V_{0(SB)}$ of the ESPVR based on an equation $$V_{0(SB)-AOP} = \frac{[A_o P_{DIA} \times ESV / (0.9 \times A_o P_{SYS}) - EDV \times E_N(t_N)]}{[A_o P_{DIA} / (0.9 \times A_o P_{SYS}) - E_N(t_N)]},$$

means for estimating a slope $E_{max(SB)}$ based on an equation $$E_{max(SB)-AOP} = (0.9 \times A_o P_{SYS})/(ESV - V_{0(SB)}).$$

* * * * *